US008613850B2

(12) United States Patent
Lin et al.

(10) Patent No.: US 8,613,850 B2
(45) Date of Patent: Dec. 24, 2013

(54) ELECTROCHEMICAL QUANTITATIVE ANALYSIS SYSTEM AND METHOD FOR THE SAME

(75) Inventors: Yueh-Hui Lin, Hsinchu (TW); Guan-Ting Chen, Tanzi Shiang (TW); Te-Ho Chen, Kaohsiung (TW); Ching-Yuan Chu, Hsinchu (TW); Jui-Ping Wang, Hsinchu (TW); Cheng Allen Chang, Hsinchu (TW); Thomas Y. S. Shen, Hsinchu (TW)

(73) Assignee: Apex Biotechnology Corp., Hsinchu Science-Based Industrial Park, Hsinchu (TW)

( * ) Notice: Subject to any disclaimer, the term of this patent is extended or adjusted under 35 U.S.C. 154(b) by 1049 days.

(21) Appl. No.: 12/234,659

(22) Filed: Sep. 21, 2008

(65) Prior Publication Data
US 2009/0078588 A1 Mar. 26, 2009

(30) Foreign Application Priority Data

Sep. 21, 2007 (TW) .............................. 96135313 A

(51) Int. Cl.
*G01N 27/327* (2006.01)

(52) U.S. Cl.
USPC ................... 205/792; 205/777.5; 204/403.02; 204/403.04

(58) Field of Classification Search
USPC ............. 204/403.01–403.15; 205/777.5, 778, 205/792
See application file for complete search history.

(56) References Cited

U.S. PATENT DOCUMENTS

| 5,120,420 | A | * | 6/1992 | Nankai et al. | 204/403.11 |
| 5,126,034 | A | * | 6/1992 | Carter et al. | 204/403.05 |
| 5,384,028 | A | * | 1/1995 | Ito | 257/253 |
| 5,997,817 | A | * | 12/1999 | Crismore et al. | 204/403.1 |
| 6,837,976 | B2 | * | 1/2005 | Cai et al. | 204/403.14 |
| 7,144,485 | B2 | * | 12/2006 | Hsu et al. | 204/403.02 |
| 2003/0042150 | A1 | * | 3/2003 | Ryu et al. | 205/778 |
| 2004/0050694 | A1 | | 3/2004 | Yang et al. | |
| 2004/0217019 | A1 | | 11/2004 | Cai et al. | |
| 2005/0019953 | A1 | * | 1/2005 | Groll | 436/514 |
| 2005/0023137 | A1 | * | 2/2005 | Bhullar et al. | 204/403.1 |
| 2007/0138026 | A1 | * | 6/2007 | Fujiwara et al. | 205/777.5 |

FOREIGN PATENT DOCUMENTS

| TW | 559660 | 11/2003 |
| TW | M288928 | 9/2005 |
| WO | WO 01/71328 | 9/2001 |

* cited by examiner

*Primary Examiner* — Alex Noguerola
(74) *Attorney, Agent, or Firm* — Snell & Wilmer L.L.P.

(57) ABSTRACT

A system for electrochemical quantitative analysis is provided. The system includes a measuring apparatus having a plurality of analysis modes. Each of the analysis modes is for quantitatively analyzing different biochemical substance. The system further includes a plurality of test strips. Each of the test strips has a different identification component for a different analysis mode. When one of the plurality of test strips is selected to electronically connect to the measuring apparatus, the measuring apparatus executes one of the plurality of analysis modes according to the identification component of the selected test strip to quantitatively analyze a corresponding biochemical substance.

18 Claims, 12 Drawing Sheets

300

ELECTROCHEMICAL QUANTITATIVE ANALYSIS SYSTEM AND METHOD FOR THE SAME

FIELD OF INVENTION

The present invention relates to an electrochemical quantitative analysis system, and more particularly to an electrochemical quantitative analysis system having identification function.

BACKGROUND OF THE INVENTION

The advance of the economy and the civilization has brought in a series of diseases, for example, Alzheimer's disease, cancer, hepatitis, hyperlipidemias, diabetes, cardiology, renal failure, gout, and apoplexy. To realize the symptoms of such diseases personally, the Point-of-Care (POCT) products have been paid close attention for a long time. With the POCT products, people can check the physical condition at anytime, anyplace. To fit in with the market requests, such self-testing products tend to be fast, cheap, and small, without requiring further help about the operation.

There are still many disadvantages for the conventional electrochemical analysis systems. One disadvantage is that the general electrochemical analysis systems provide one-to-one analyses only. For example, the blood sugar analysis test strip used with the blood sugar analysis apparatus cannot be applied to analyze other biochemical substance, for example, cholesterol. Therefore, it is not practical using such analysis systems to analyze multiple biochemical substances at the same time. To overcome the above problem, some systems will integrate apparatuses for multiple biochemical substances into the same unit. However, users still have to manually switch to a proper analysis mode corresponding to the desired biochemical substance. This may be regarded as an extra operation burden.

The other disadvantage is that a whole blood sample can be, for example, used for analyzing certain biochemical substances, for example, cholesterol. This can be referred to systems mentioned in U.S. Pat. Nos. 5,120,420, 5,762,770, and Taiwan Patent No. 124332. The blood cells in the whole blood sample will obviously interfere with the cholesterol electrochemical reaction. Therefore, before analyzing those biochemical substances in the conventional systems, the whole blood sample has to be processed in advance. To overcome the above problems, some inventions try to integrate a pre-treatment device to exclude the blood cells from a whole blood sample. These inventions are referred to in U.S. Pat. Nos. 6,033,866 and 6,436,255. However, such systems are not practical because of the complicated operation and the necessary amount of blood. Besides the blood cells, the whole blood sample contains other components, for example, uric acid, vitamin C, or acetaminophen. These components will also impact the electrochemical analysis results for certain biochemical substances.

Accordingly, it is advantageous to have a novel electrochemical quantitative analysis system to overcome the limitations of the conventional technology.

SUMMARY OF THE INVENTION

One aspect of the present invention is to provide a test strip with an identification component. The measuring apparatus can automatically switch to an analysis mode according to the test strip to avoid an operation burden.

In one embodiment, the present invention provides an electrochemical quantitative analysis system including a measuring apparatus and a plurality of test strips. The measuring apparatus has a plurality of analysis modes and different analysis modes are for quantitatively analyzing different biochemical substances. Different test strips have different identification components corresponding to different analysis modes. When one of the test strips is selected to electronically connect to the measuring apparatus, the measuring apparatus executes an analysis mode according to the identification component of the test strip to quantitatively analyze a corresponding biochemical substance.

Another aspect of the present invention is to provide a test strip with two working electrodes. One of the working electrodes is for measuring an electrochemical reaction current related to a substance to be tested. The other working electrode is for measuring an electrochemical reaction current related to the potential interfering substances rather than substance to be tested. Such current from the other working electrode can be named as background reaction current. Then, the measuring apparatus can correct a quantitative analysis result according to a current difference between these two working electrodes. Therefore a whole blood sample can be applied to the present invention. This can get rid of the need for pre-processing the whole blood sample in the conventional technology.

In another embodiment, the present invention provides an electrochemical quantitative analysis system including a measuring apparatus and a plurality of test strips. The measuring apparatus has a plurality of analysis modes and different analysis modes are for quantitatively analyzing different biochemical substance. Different test strips have different identification components corresponding to different analysis modes. One of the test strips further includes a first working electrode for producing a first current signal and a second working electrode for producing a second current signal. The measuring apparatus corrects a quantitative analysis result for the corresponding biochemical substance according to a difference between the first current signal and the second current signal.

Still another aspect of the present invention is to provide a test strip with three working electrodes. The first working electrode is for measuring an electrochemical reaction current of a substance to be tested. The second working electrode is for measuring a background reaction current. The third working electrode is for measuring a quantity of certain interfering substances contained in the sample. The certain interfering substances often have nonlinear impacts on the electrochemical reaction current of the material to be tested, for example, the impact of the HCT % (hematocrit, HCT) on the electrochemical reaction current of blood sugar. The measuring apparatus can correct a quantitative analysis result according to a current difference among these three working electrodes. Therefore a whole blood sample can be applied to the present invention. This can get rid of the need for conventional technology pre-processing the whole blood sample.

DETAILED DESCRIPTION OF THE INVENTION

The present invention discloses an electrochemical quantitative analysis system, which has a test strip containing an identification component to automatically trigger a specific analysis mode corresponding to the test strip. In this way, the operation is easy to users. The present invention also includes an improved correction mode to obtain accurate quantitative analysis results. The present invention will be more readily appreciated by referring to the following detailed description with the accompanying figures. It should be noted that the similar components in the accompanying figures use the similar symbols. To clarify the present invention more clearly, each component in the accompanying figures may not be illustrated in scale. To avoid obscuring the present invention, the conventional components, materials, and technologies are abbreviated in the following description. It should be understood that the following embodiments are for illustration only, not for limitation to the scope of the present invention.

Figure 1A:
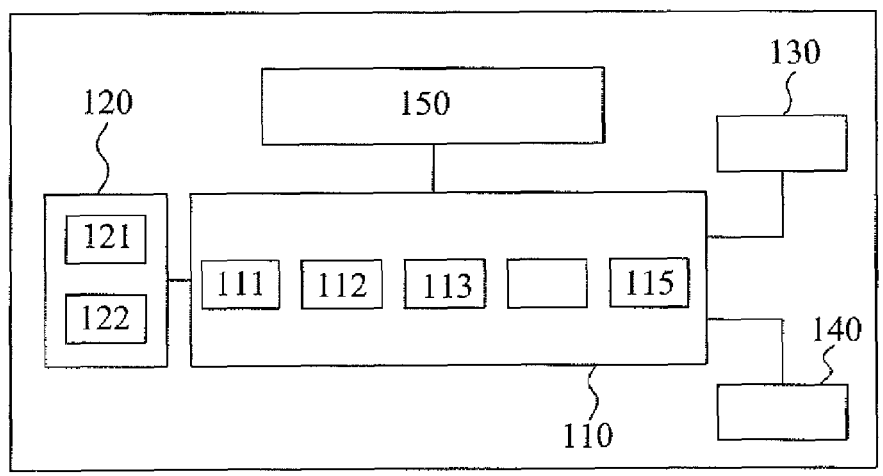
FIG. 1A illustrates a measuring apparatus according to an embodiment of the present invention.
Figure 1B:
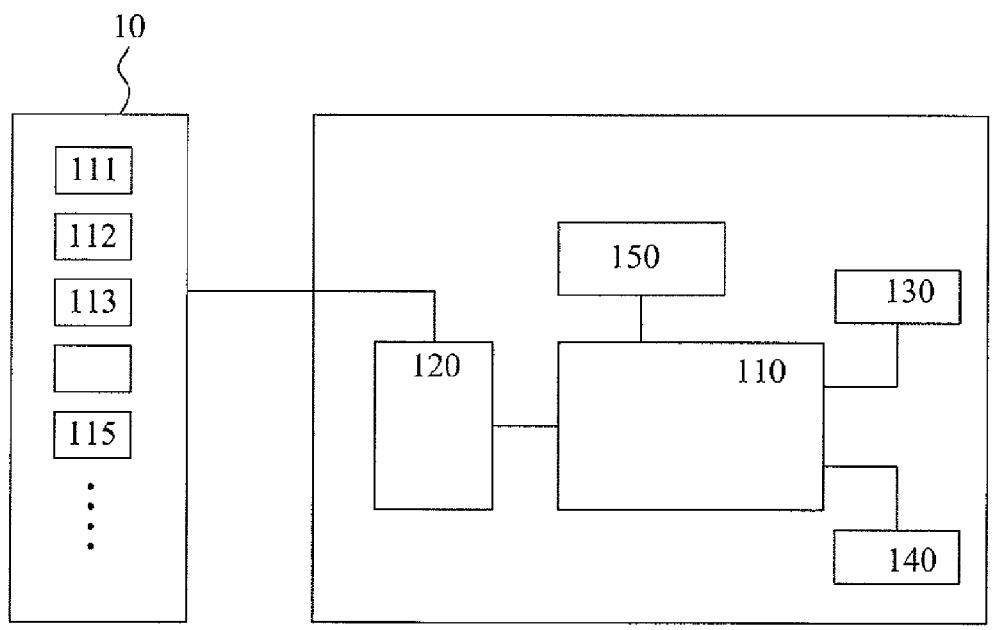
FIG. 1B illustrates an external card connected to a measuring apparatus according to an embodiment of the present invention.

The electrochemical quantitative analysis system of the present invention includes a measuring apparatus and a plurality of test strips. FIG. 1A illustrates a measuring apparatus. FIG. 1B illustrates an external card connected to a measuring apparatus. FIG. 2A-2B, FIG. 3A-3B, FIG. 4-6, and FIG. 7A-7B illustrate several test strips.

Referring to FIGS. 1A and 1B, the measuring apparatus 100 of the present invention includes a processor 110, a memory 120, a display 130, a temperature sensor 140, and a connector 150. The processor 110 can have a plurality of analysis modes, for example, cholesterol analysis mode 111, blood sugar analysis mode 112, lactic acid analysis mode 113, and uric acid analysis mode 115. Each analysis mode is for quantitatively analyzing a corresponding biochemical substance. Such analysis modes can be stored in the processor 110 as firmware, as shown in FIG. 1A. These analysis modes can also be stored in an external card 10 or other suitable electrical device, as shown in FIG. 1B. Through the electrical connection with the measuring apparatus 100, these analysis modes can be transmitted from the external card 10 to the measuring apparatus 100. There is no limitation to the number of analysis modes in the external card 10. For example, the external card 10 can have only one analysis mode. There is also no limitation to the number of analysis modes in the measuring apparatus 100. For example, the measuring apparatus 100 can have only one analysis mode. The memory 120 is used for storing any data, for example, measuring data, analysis results, or the analysis modes mentioned above. The memory 120 shown in FIG. 1A includes certain correction modes for the processor 110 to correct the measuring data. These correction modes, for example, temperature correction mode 121 and HCT % correction mode 122, can be stored in the external card 10. The temperature sensor 140 is for detecting the environment temperature when the analysis is in process. The processor 110 will compare the difference between the environment temperature and the standard temperature and use temperature correction mode 121 to correct the analysis result, and then display the analysis result on the display 130. The connector 150 is used for the electrical connection between the measuring apparatus 100 and the test strip (described later). For example, the connector 150 can include a socket containing several contact points for the connection to each electrode of the test strip. When the test strip is plugged into the socket, the measuring apparatus 100 can provide power to the test strip and transmit the measuring data back to the processor 110 for analysis. Preferably, the connector 150 is suitable for each test strip of the present invention, and then the measuring apparatus 100 doesn't need other sockets to electrically connect to other test strips.

Figure 2A:
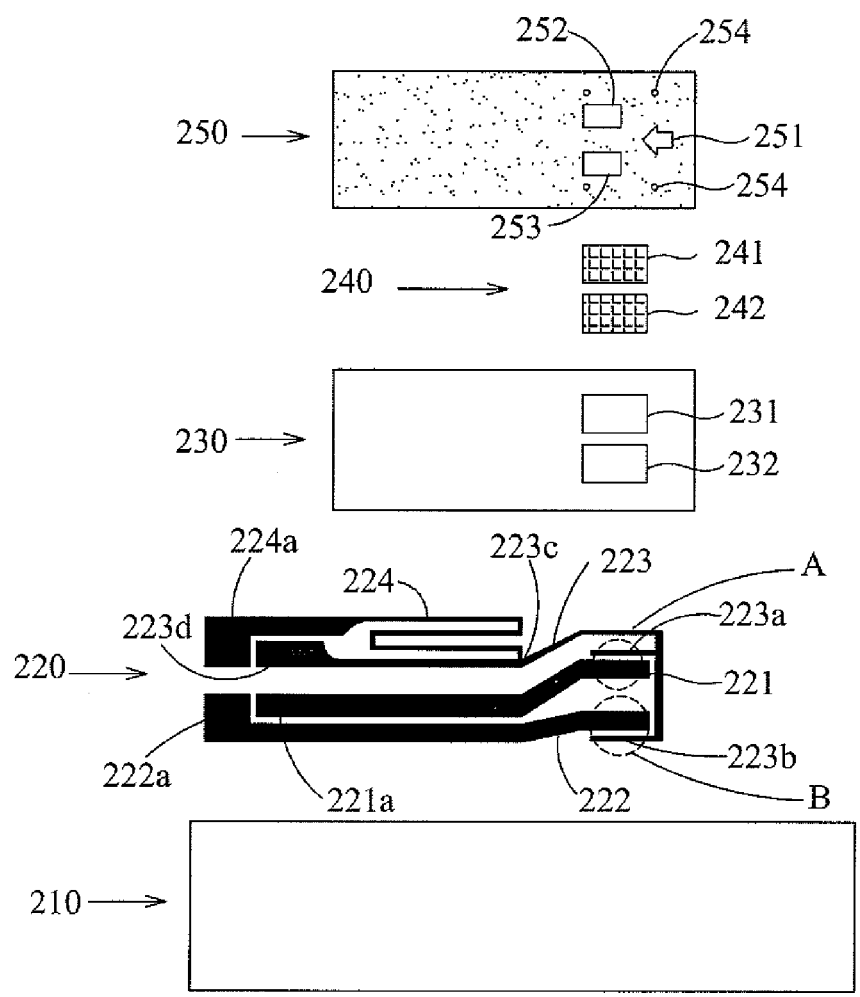
FIG. 2A-2B illustrate a first test strip before and after assembling according to an embodiment of the present invention.
Figure 2B:
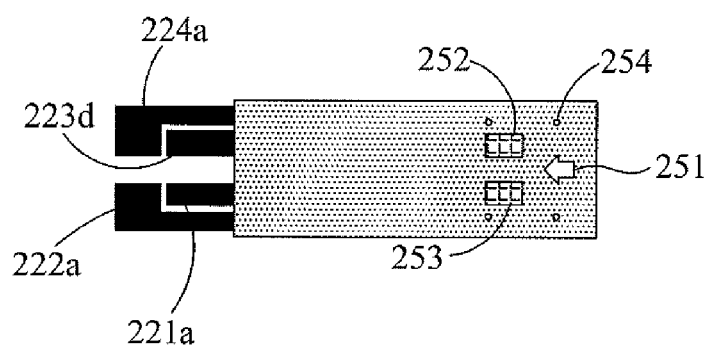

FIG. 2A and FIG. 2B respectively illustrates a first test strip 200 before and after assembling. In this embodiment, the first test strip 200 is used for analyzing a quantity of cholesterol contained in the sample. The first test strip 200 includes a substrate 210, a circuit 220, an isolation layer 230, a reaction compound 240 and an upper cover 250. The substrate 210 can be formed by general isolated plastic, for example, PE or PVC. The circuit 220 is formed on the substrate 210. The material used for the circuit 220 can be any kind of conductive materials. The circuit 220 includes a first working electrode 221, a second working electrode 222, a reference electrode 223, and an identification component 224. The first working electrode 221, the second working electrode 222, and the reference electrode 223 are isolated from one another. The reference electrode 223 is connected to the identification component 224. The first working electrode 221, the second working electrode 222 and the identification component 224 respectively have a first working electrode joint 221a, a second working electrode joint 222a, and an identification component joint 224a, for an electrical connection with the connector 150. One side of the reference electrode 223 can be divided into a first part 223a and a second part 223b, respectively close to the first working electrode 221 and the second working electrode 222, to form an electrochemical reaction area A and B. The other side of the reference electrode 223 can be divided into a third part 223c and a reference electrode joint 223d. The third part 223c is connected to the identification component 224. The reference electrode joint 223d is used for an electrical connection with the connector 150. The identification component 224 can be a passive device, for example, a transistor, an inductor, or a capacitor. The identification component 224 has a specific electrical characteristic corresponding to a specific analysis mode of the measuring apparatus 100. When the identification component 224 is electrically connected to the measuring apparatus 100, the processor 110 will read out this specific electrical characteristic to trigger this specific electrical analysis mode.

Referring to FIGS. 2A and 2B, the isolation layer 230 is formed above the circuit 220. The material for the isolation layer 230 is similar to the material used in the substrate 210. The size of the isolation layer 230 should be smaller than the occupied area of the circuit 220, such that the first working electrode joint 221a, the second working electrode joint 222a, the reference electrode joint 223d, and the identification component joint 224a will not be blocked by the isolation layer 230. The isolation layer 230 has two openings, corresponding to the electrochemical reaction areas A and B, as a first reaction basin 231 and a second reaction basin 232, to deposit the reaction compound 240. The composition of the reaction compound 240 is decided according to the corresponding biochemical substance of the first test strip 200. In detail, the reaction compound 240 can be divided into a first reaction compound 241 and a second reaction compound 242, respectively deposited to the first reaction basin 231 and the second reaction basin 232. The first reaction compound 241 has an enzyme for reacting with the corresponding biochemical substance to be tested contained in the sample. The second reaction compound 242 doesn't have the enzyme. In other words, the second reaction compound 242 is a reference group of the first reaction compound 241. The second reaction compound 242 can measure a current produced from the other substances (rather than the substance to be tested). The current can be named as background current. The background current can be used for the processor 110 to correct an analysis result. Therefore, the system of the present invention is suitable for a whole blood sample without the need for the pre-process procedure. The system can also deduct an interfering current from some interfering substances from the whole blood sample.

It should be noted that the reaction compound 240 composition and the enzyme type are related to the corresponding biochemical substance of the first test strip 200. And the people in the art have already known the composition for the reaction compound 240 and the type for the enzyme. For example, if the biochemical substance to be tested is uric acid, refer to U.S. Pat. No. 6,258,230 for the composition of the reaction compound 240 and the type of the enzyme; if the biochemical substance to be tested is cholesterol, then refer to U.S. patent application Ser. No. 10/441,249 for the same. Besides, the reaction compound 240 can have hydrophile carriers, for example, carboxymethyl cellulose or polyethylene oxide. When the sample is deposited, such hydrophile carriers can help produce capillarity effect to promote uniform reaction.

Referring to FIGS. 2A and 2B again, the upper cover 250 covers the isolation layer 230 and the reaction compound 240. As shown in the figures, the upper cover 250 includes a sample placement area 251, and observation windows 252, 253 corresponding to the first reaction basin 231 and the second reaction basin 232 for observing whether the samples successfully get into the reaction basins from the sample placement area 251. Besides, the upper cover 250 further includes several vents 254 near the sample placement area 251, and observation windows 252, 253, to prevent production of bubbles. The material and size of the upper cover 250 are similar to the isolation layer 230.

Figure 3A:
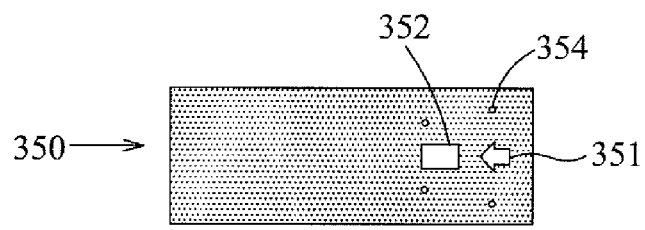
FIG. 3A-3B illustrate a second test strip before and after assembling according to an embodiment of the present invention.
Figure 3A:
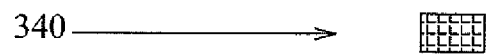
Figure 3A:
Figure 3A:
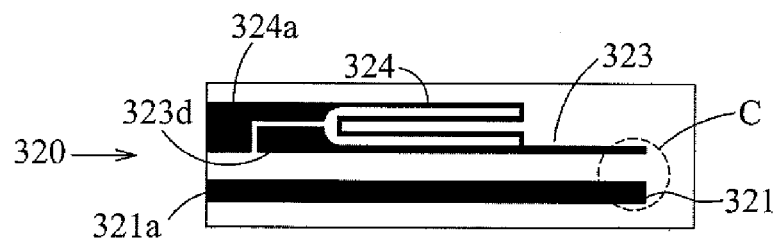
Figure 3A:
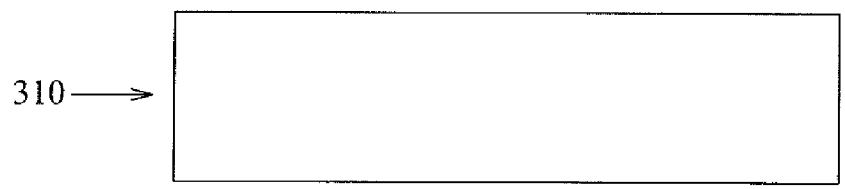
Figure 3B:
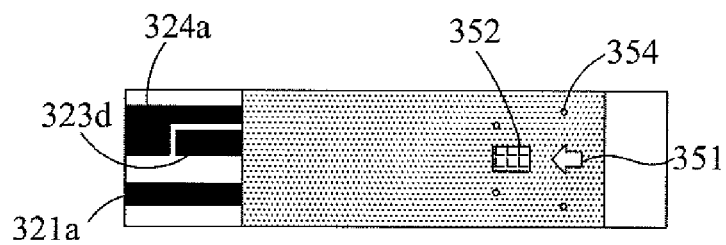

Besides the first test strip 200 (two working electrodes) mentioned above, the present invention also includes a second test strip 300 having only one working electrode, as shown in FIGS. 3A and 3B. The second test strip 300 is for analyzing specific biochemical substance, which doesn't need to deduct interfering reaction. As shown in the figures, the second test strip 300 includes a substrate 310, a circuit 320, an isolation layer 330, a reaction compound 340 and an upper cover 350. The circuit 320 includes a working electrode 321, a reference electrode 323, and an identification component 324. The working electrode 321 and the reference electrode 323 are isolated from one another. The reference electrode 323 is connected to the identification component 324. The working electrode 321 and the identification component 324 respectively have a working electrode joint 321a and an identification component joint 324a, for an electrical connection with the connector 150. One side of the reference electrode 323 is close to the working electrode 321 to form an electrochemical reaction area C. The other side of the reference electrode is connected to the identification component 324; therefore the measuring apparatus can be selectively connected to the reference electrode 323 through the identification component 324. The reference electrode 323 has a reference electrode joint 323d for an electrical connection with the connector 150. The identification component 324 has similar characteristics as mentioned above. The identification component 324 can be a passive device, for example, a transistor, an inductor, or a capacitor, which has a specific electrical characteristic corresponding to a specific analysis mode of the measuring apparatus 100. When the identification component 324 is electrically connected to the measuring apparatus 100, the processor 110 will read out this specific electrical characteristic to trigger this specific electrical analysis mode.

Referring to FIGS. 3A and 3B, the size of the isolation layer 330 should be smaller than the occupied area of the circuit 320, such that the working electrode joint 321a, the reference electrode joint 323d, and the identification component joint 324a will not be blocked by the isolation layer 330. The isolation layer 330 has one opening, corresponding to the electrochemical reaction area C, as a reaction basin 331 to deposit the reaction compound 340. The upper cover 350 covers the isolation layer 330 and the reaction compound 340. As shown in the figures, the upper cover 350 includes a sample placement area 351 and an observation window 352 corresponding to the reaction basin 331. Besides, the upper cover 350 further includes several vents 354 near the sample placement area 351 and observation windows 352. The materials of the substrate 310, the circuit 320, the isolation layer 330, and the upper cover 350 are similar to the above description for the test strip 200.

Figure 4:
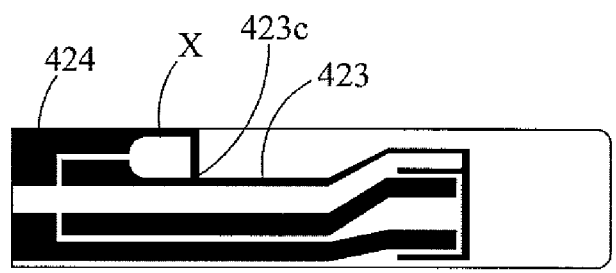
FIG. 4 illustrates a third test strip according to an embodiment of the present invention.
Figure 5:
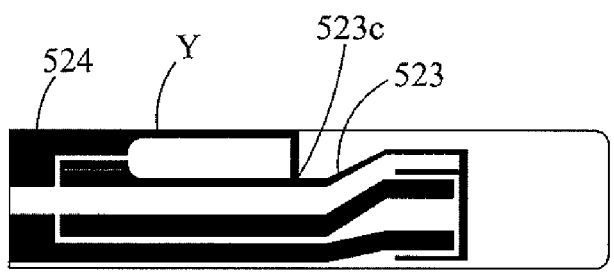
FIG. 5 illustrates a forth test strip according to an embodiment of the present invention.
Figure 6:
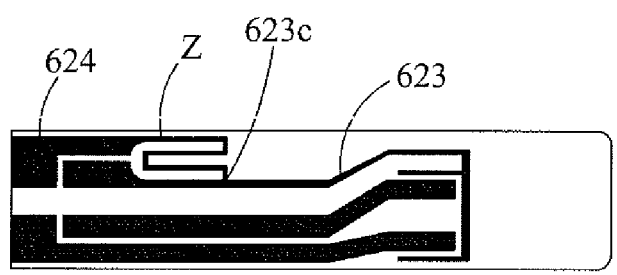
FIG. 6 illustrates a fifth test strip according to an embodiment of the present invention.

Besides the first test strip 200 and the second test strip 300 mentioned above, the present invention also includes other test strips having different identification components and reaction compounds, such as the third test strip 400, the forth test strip 500 and the fifth test strip 600 shown in the FIG. 4, FIG. 5, and FIG. 6 respectively. In these figures, the isolation layers, reaction compounds, and the upper covers are removed to clearly indicate the particular features of each of the identification components 424, 524, and 624. In detail, each of the identification components 424, 524, and 624 is respectively connected to its reference electrode 423, 523, and 623 through the contact 423c, 523c, and 623c. It should be understood that the identification components 424, 524, and 624 are various transistors with different patterns X, Y, and Z, which can represent different resistances such that the processor 110 can read and identify them. In addition to different patterns, it should be noted that different thicknesses, sizes, lengths, or materials of the lines of the circuit could be used to represent different resistances. In addition to the transistor, each of the identification components 424, 524 and 624 can be other passive device, for example, an inductor or a capacitor.

Figure 7A:
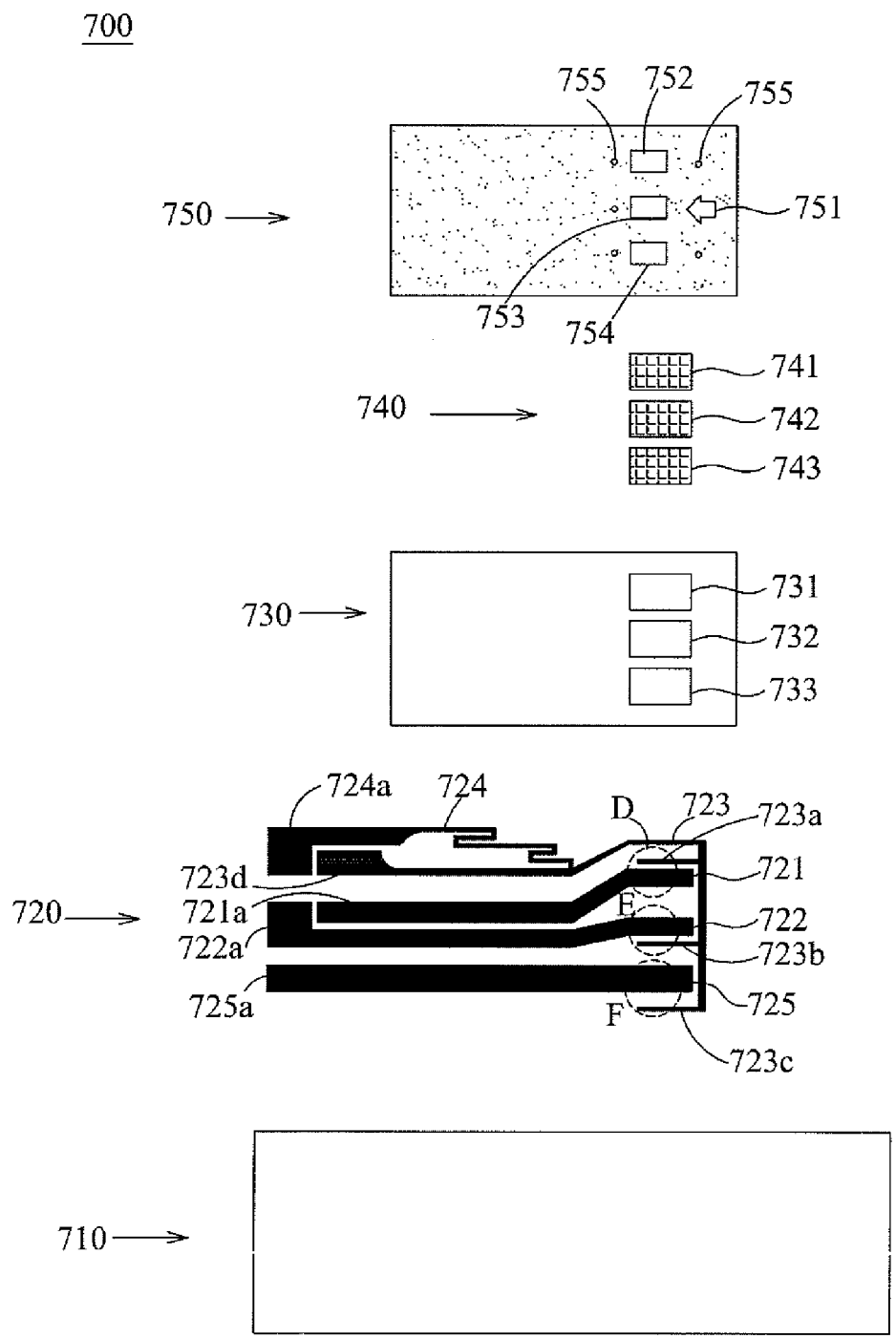
FIG. 7A-7B illustrate a sixth test strip before and after assembling according to an embodiment of the present invention.
Figure 7B:
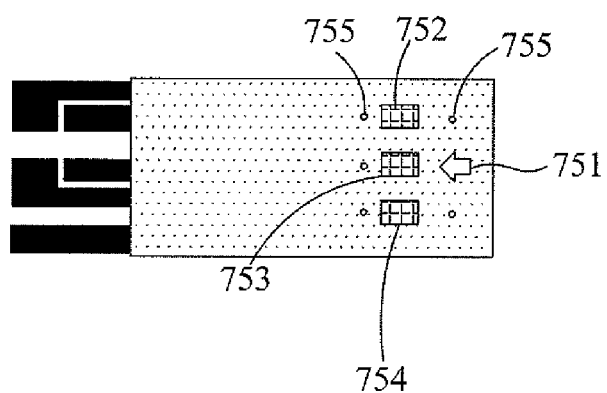

FIGS. 7A and 7B illustrate the sixth test strip of the present invention. The difference between the sixth test strip and the test strips mentioned above is that the sixth test strip has a third reaction basin for analyzing a quantity of certain interfering substances contained in a whole blood sample. Such interfering substances often have nonlinear impacts on the electrochemical reaction current of a substance to be tested, for example, the HCT % to the electrochemical reaction current of blood sugar. In this embodiment, the sixth test strip is for analyzing the quantity of the blood sugar contained in the sample; and the third reaction basin is for analyzing the HCT % contained in the sample to correct the measured blood sugar values.

As shown in the FIGS. 7A and 7B, the sixth test strip 700 includes a substrate 710, a circuit 720, an isolation layer 730, a reaction compound 740 and an upper cover 750. The circuit 720 includes a first working electrode 721, a second working electrode 722, a third working electrode 725, a reference electrode 723, and an identification component 724. The first working electrode 721, the second working electrode 722, the third working electrode 725, and the reference electrode 723 are isolated from one another. The reference electrode 723 is connected to the identification component 724. The first working electrode 721, the second working electrode 722, the third working electrode 725, and the identification component 724 respectively has a first working electrode joint 721a, a second working electrode joint 722a, a third working electrode joint 725a, and an identification component joint 724a, for an electrical connection with the connector 150. One side of the reference electrode 723 can be divided into a first part 723a, a second part 723b, and a third part 723c, respectively close to the first working electrode 721, the second working electrode 722, and the third working electrode 725, to form an electrochemical reaction area D, E, and F. The other side of the reference electrode 723 can be divided into a forth part 723f and a reference electrode joint 723d. The forth part 723f is connected to the identification component 724. Similar to the above mention, the identification component 724 has a specific electrical characteristic corresponding to a specific analysis mode of the measuring apparatus 100. When the identification component 724 is electrically connected to the measuring apparatus 100, the processor 110 will read out this specific electrical characteristic to trigger the specific electrical analysis mode.

Further referring to FIGS. 7A and 7B, the isolation layer 730 is formed above the circuit 720. The size of the isolation layer 730 should be smaller than the occupied area of the circuit 720, such that each electrode joint 721a, 722a, 725a, 724a, and 723d will not be blocked by the isolation layer 730. The isolation layer 730 respectively forms a first reaction basin 731, a second reaction basin 732, and a third reaction basin 733 at the electrochemical reaction area D, E, and F to deposit the reaction compound 740. The composition of the reaction compound 740 is decided according to the corresponding biochemical substance of the sixth test strip 700. In detail, the reaction compound 740 can be divided into a first reaction compound 741, a second reaction compound 742, and a third reaction compound 743 respectively. The first reaction compound 741 has an enzyme for reacting with the corresponding biochemical substance to be tested contained in the sample. The second reaction compound 742 doesn't have the enzyme. In other words, the second reaction compound 742 is a reference group of the first reaction compound 741. Referring to the U.S. patent application Ser. No. 09/771634, the third reaction compound 743 includes a chemical component to test the HCT %.

Referring back to FIGS. 7A and 7B, the upper cover 750 covers the isolation layer 730 and the reaction compound 740. As shown in the figures, the upper cover 750 includes a sample placement area 751, observation windows 752, 753, and 754 corresponding to each of the reaction basins 731, 732, and 733. Besides, the upper cover 750 further includes several vents 755, near the sample placement area 751 and observation windows 752, 753 and 754, to prevent from producing bubbles.

Through the above illustration, it should be understood that the present invention provides an electrochemical quantitative analysis system, including a measuring apparatus 100 having a plurality of analysis modes, for example, cholesterol analysis mode 111, blood sugar analysis mode 112, lactic acid analysis mode 113, uric acid analysis mode 115, and HCT % correction mode 122. The measuring apparatus 100 also has a plurality of test strips, for example, the first test strip to the sixth test strip. Each test strip has different identification component 224, 324, 424, 524, 624, and 724 corresponding to specific one or multiple analysis modes.

Figure 8:
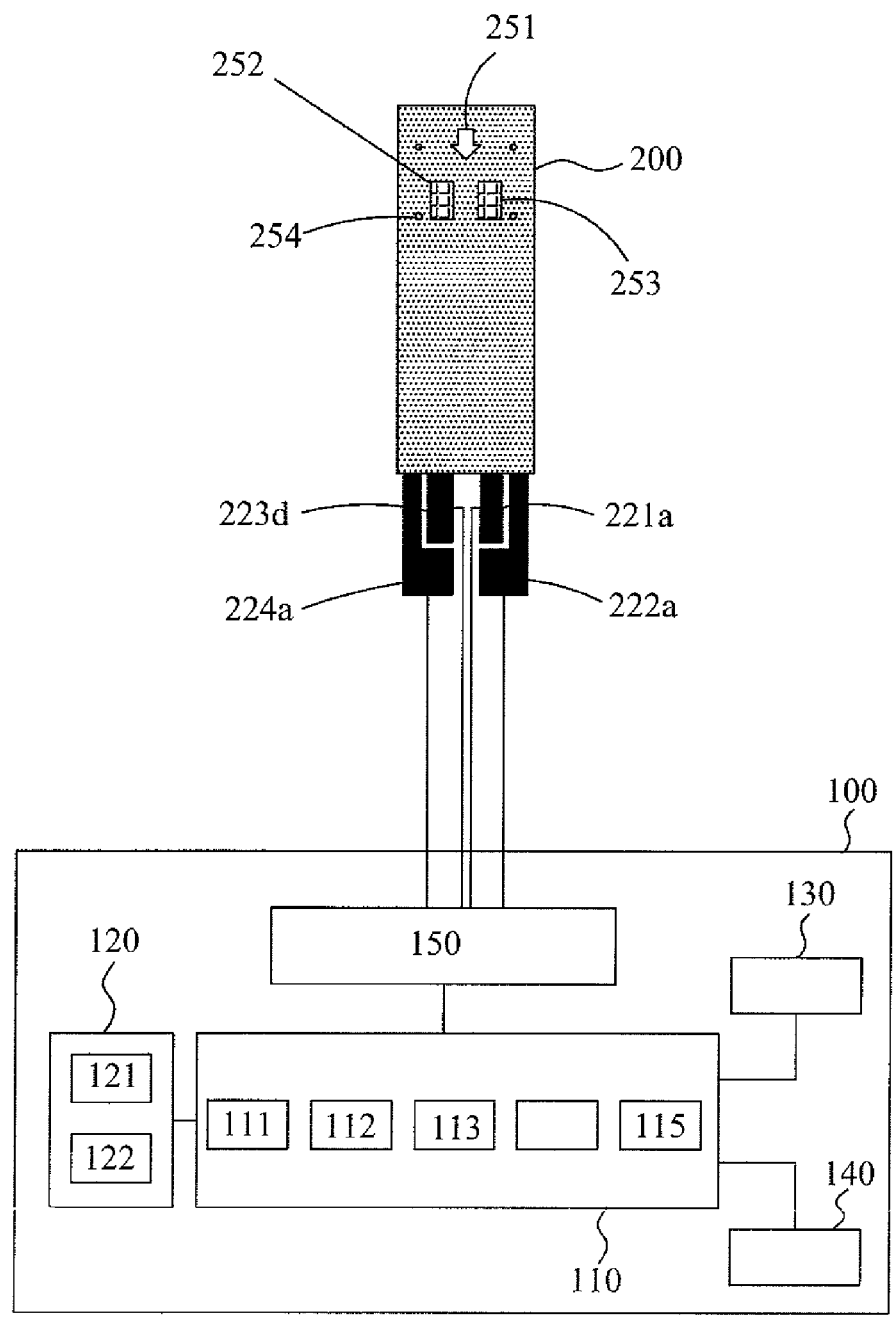
FIG. 8 illustrates a first test strip connected to a measuring apparatus according to an embodiment of the present invention.

For example, as shown in FIG. 8, the user can select the first test strip 200 for analyzing a quantity of cholesterol contained in the blood. Then a whole blood sample is deposited at the sample placement area of the first test strip 200. And then the first test strip 200 is connected with the connector 150 of the measuring apparatus 100. Meanwhile, the processor 110 will trigger the cholesterol analysis mode 111 according to the electrical characteristic of the identification component 224 of the first test strip 200. Also, the processor 110 will sense a first current signal and a second current signal generated respectively from the first working electrode 221 and the second working electrode 222. The processor calculates a draft quantity of the cholesterol contained in the whole blood sample according to the first current signal. Then the processor corrects the draft quantity to obtain a more accurate cholesterol quantity according to the difference between the first current signal and the second signal. The third test strip 400 can be selected to analyze a quantity of lactic acid contained in the blood. Similarly, the processor 110 will automatically trigger the lactic acid analysis mode 113 according to the electrical characteristic of the identification component 424 of the third test strip 400 without further operation done by the user to see whether the analysis mode is suitable. Again, the sixth test strip 700 can be selected to analyze a quantity of blood sugar with the HCT % correction. Similarly, the processor 110 will automatically trigger the blood sugar analysis mode 112 and the HCT % correction mode 122 according to the electrical characteristic of the identification component 724 of the sixth test strip 700.

Figure 9:
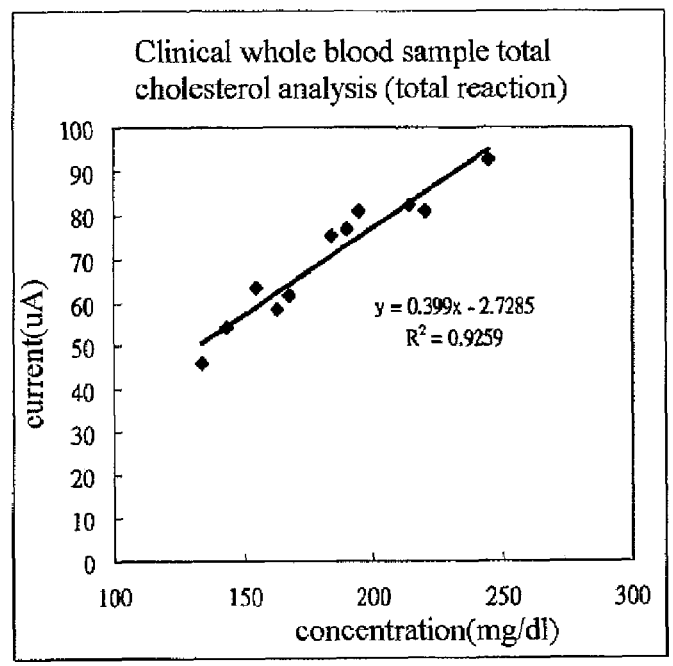
FIG. 9 is a cholesterol concentration vs. current chart according to a plurality of first test strip analysis results before correction.
Figure 10:
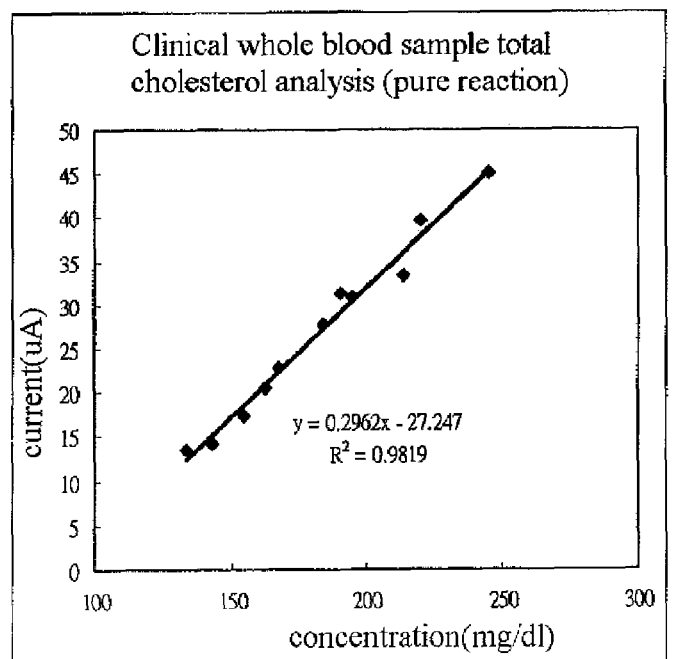
FIG. 10 is a cholesterol concentration vs. current chart according to a plurality of first test strip analysis results after correction.

FIG. 9 and FIG. 10 respectively illustrate a cholesterol concentration vs. current chart according to a plurality of first test strip 200 analysis results before and after correction. FIG. 9 and FIG. 10 can demonstrate the accuracy of the correction. It should be noted that the $R^2$ value in FIG. 9 is 0.9259, and the $R^2$ value in FIG. 10 is 0.9819. In FIG. 9, the second current signal is not deducted from the current data. In FIG. 10, the second current signal has been deducted. As know to the people in the art, $R^2$ value can represent the accuracy of the cholesterol concentration and higher $R^2$ values represent higher accuracy.

Figure 11:
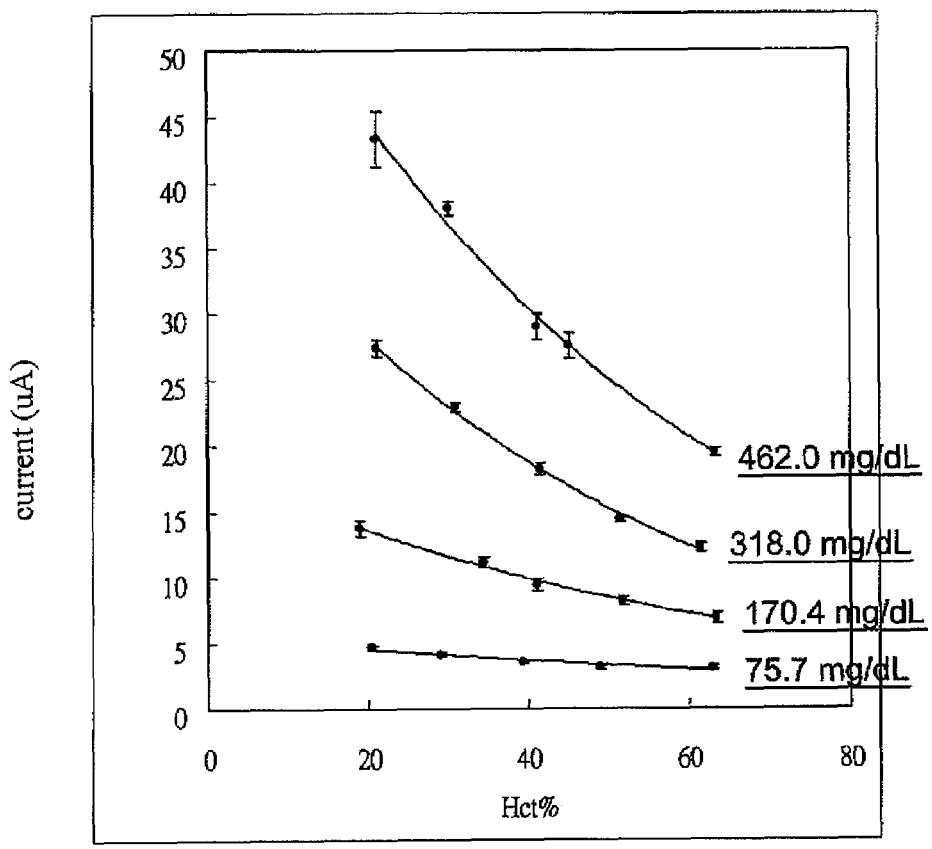
FIG. 11 is a HCT % vs. current chart according to a plurality of sixth test strip analysis results for whole blood samples with known blood sugar concentrations.

FIG. 11 illustrates a HCT % vs. current chart according to a plurality of sixth test strip 700 analysis results for whole blood samples with known blood sugar concentrations (respectively for 75.7 mg/dL, 170.4 mg/dL, 318.0 mg/dL, and 462.0 mg/dL). FIG. 11 indicates the higher the blood sugar concentrations, the higher the difference between the current values corresponding to different HCT %, which means that at higher concentration of the blood sugar, the current values are impacted by the variations of HCT % more easily. The mathematical relation between the known blood sugar values, current values, and the HCT % shown in the FIG. 11 can be represented as:

Blood sugar value (mg/dL)=$Ae^{-BX}$, wherein $R^2$ is 0.909~0.997.

In the above relation, A and B stand for specific constants for different concentrations, and X stands for HCT %. The data of the uncorrected current values and the HCT % for each known blood sugar concentrations shown in FIG. 11 can be stored in the HCT % correction mode 122. The processor 110 can process the uncorrected currents with optimum correction according to the data. Table 1 illustrates two whole blood samples with known blood concentration 200 mg/dL and 258 mg/dL, which are analyzed by the sixth test strip 700 and the measuring apparatus 100 of the present invention to respectively obtain the uncorrected blood sugar values and the corrected values. From Table 1, the corrected blood sugar values have higher accuracy.

TABLE 1

| Known | | Uncorrected | | Corrected | |
|---|---|---|---|---|---|
| Blood Sugar | HCT % | Measured Blood Sugar | Error | Measured Blood Sugar | Error |
| 200 | 31 | 244 | 22% | 217.7 | 8.9% |
| 258 | 33 | 292 | 13% | 266.7 | 3.4% |

Accordingly, the electrochemical quantitative analysis system of the present invention utilizing multiple basin electrochemical reactions can remove the linear current interfering effects from the interfering substances as well as processing the post correction for other nonlinear interfering effects. Therefore an accurate concentration value for a specific biochemical substance of the whole blood sample can be obtained without the pre-process to the whole blood sample.

The above illustration is for a preferred embodiment of the present invention is not limited to the claims of the present invention. Equivalent amendments and modifications without departing from the spirit of the invention should be included in the scope of the following claims.

The invention claimed is:

1. An electrochemical quantitative analysis system, comprising:
    a measuring apparatus, having a plurality of analysis modes, wherein each analysis mode is for quantitatively analyzing different biochemical substance; and
    a plurality of test strips, each test strip having a different identification component corresponding to each analysis mode, wherein when one of the plurality of test strips is selected to electronically connect to the measuring apparatus, the measuring apparatus executes the analysis mode according to the identification component of the test strip to quantitatively analyze a corresponding biochemical substance, and wherein each test strip comprises:
        a first working electrode, for producing a first current signal in a first reaction area;
        a second working electrode, for producing a second current signal in a second reaction area different from the first reaction area; and
        a reference electrode, one side of the reference electrode being divided into a first part and a second part to respectively form a first reference electrode corresponding to the first reaction area and a second reference electrode corresponding to the second reaction area, and the other side of the reference electrode being divided into a reference electrode joint and a third part connected to the identification component.

2. The system according to claim 1, wherein the measuring apparatus is selectively connected to each test strip through a connector and the connector is suitable for each test strip.

3. The system according to claim 1, wherein each identification component comprises a passive device with different electrical characteristic and the measuring apparatus executes one of the plurality analysis modes according to the electrical characteristic.

4. The system according to claim 3, wherein the passive device is a transistor, an inductor, or a capacitor.

5. The system according to claim 3, wherein each passive device is a transistor formed by different pattern, thickness, size, length, or material.

6. The system according to claim 1, wherein the measuring apparatus is selectively connected to the reference electrode through the identification component.

7. The system according to claim 1, wherein one of the plurality analysis modes is built inside the measuring apparatus.

8. The system according to claim 1, wherein one of the plurality analysis modes is stored in an external card.

9. The system according to claim 1, wherein the measuring apparatus corrects a quantitative analysis result for the corresponding biochemical substance according to a difference between the first current signal and the second current signal.

10. The system according to claim 9, wherein one of the plurality test strips further comprises:
    a first reaction basin on the first working electrode, the first reaction basin containing an enzyme for reacting with the corresponding biochemical substance; and
    a second reaction basin on the second working electrode, wherein the second reaction basin doesn't contain the enzyme.

11. The system according to claim 9, wherein one of the plurality of test strips further comprises a third working electrode for producing a third current signal for the correction mode.

12. The system according to claim 1, wherein each test strip further comprises a sample placement area, an observation window, and at least one vent near to the sample placement area and the observation window.

13. The system according to claim 1, wherein the electrochemical quantitative analysis system is suitable for a whole blood sample.

14. The system according to claim 1, wherein the measuring apparatus comprises a correction mode to correct a quantitative analysis result for the corresponding biochemical substance.

15. The system according to claim 14, wherein the correction mode is a temperature correction mode or a HCT % correction mode.

16. A method of utilizing the system in the claim 1 for quantitatively analyzing biochemical substances, comprising:
    selecting one of the test strips to analyze the corresponding biochemical substance;
    disposing a sample into the strip; and
    electrically connecting the strip and the measuring apparatus, wherein the measuring apparatus executes the analysis mode according to the identification component of the strip to analyze a quantity of the corresponding biochemical substance contained in the sample.

17. The method according to claim 16, wherein the sample is a whole blood sample.

18. The method according to claim 16, wherein the test strip further comprises a third working electrode for producing a third current signal such that the measuring device can have a nonlinear correction of the quantity of the corresponding biochemical substance contained in the sample.

\* \* \* \* \*